United States Patent

Bhandari et al.

(10) Patent No.: US 6,962,945 B2
(45) Date of Patent: Nov. 8, 2005

(54) N-ARYLOXYPROPANOLYL-N'-PHENETHYL-UREA

(75) Inventors: Kalpana Bhandari, Lucknow (IN);
Shipra Srivastava, Lucknow (IN);
Chandeshwar Nath, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 56 days.

(21) Appl. No.: 10/811,296

(22) Filed: Mar. 26, 2004

(65) Prior Publication Data

US 2005/0215631 A1 Sep. 29, 2005

(51) Int. Cl.[7] ........................ A01N 47/28; A61K 31/17
(52) U.S. Cl. ..................... 514/595; 564/50; 564/52; 564/53; 564/54; 564/63; 654/55; 514/585; 514/588; 514/580
(58) Field of Search ................... 564/55, 54, 50, 564/52, 53, 63; 514/595, 585, 588, 580

(56) References Cited

U.S. PATENT DOCUMENTS 5,902,899 A * 5/1999 Hayashi et al. ............... 564/58

FOREIGN PATENT DOCUMENTS

| EP | 0 738 711 A1 | 10/1996 |
|---|---|---|
| EP | 0 798 291 A1 | 10/1997 |
| EP | 0 955 293 A1 | 11/1999 |
| WO | WO-00/35875 A1 | 6/2000 |

OTHER PUBLICATIONS

Srivastava et al., Journal of Organometallic Chemistry, 414 (1991), 65–69.*

* cited by examiner

Primary Examiner—Johann Richter
Assistant Examiner—Chukwuma Nwaonicha
(74) Attorney, Agent, or Firm—Darby & Darby

(57) ABSTRACT

The present invention provides N-aryloxypropanolyl-N'-phenethyl-urea derivatives of formula 3, method for their preparation and use thereof as potent appetite suppressants for treatment of obesity Formula 3

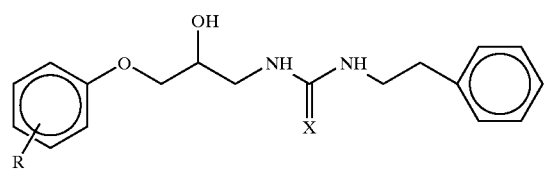

wherein R is selected from the group consisting of H, 2, 3 or 4-trifluoromethyl, 2, 3, or 4-chloro, 2, 3, or 4-bromo, 4-acetyl, 4-propionyl, 4-acetamido, 2,3 or 4 methoxy, 4 nitrile, 2,3 or 4-methyl, and 4 formyl and X is S or O.

16 Claims, 1 Drawing Sheet

N-ARYLOXYPROPANOLYL-N'-PHENETHYL-UREA

FIELD OF THE INVENTION

Figure 1:
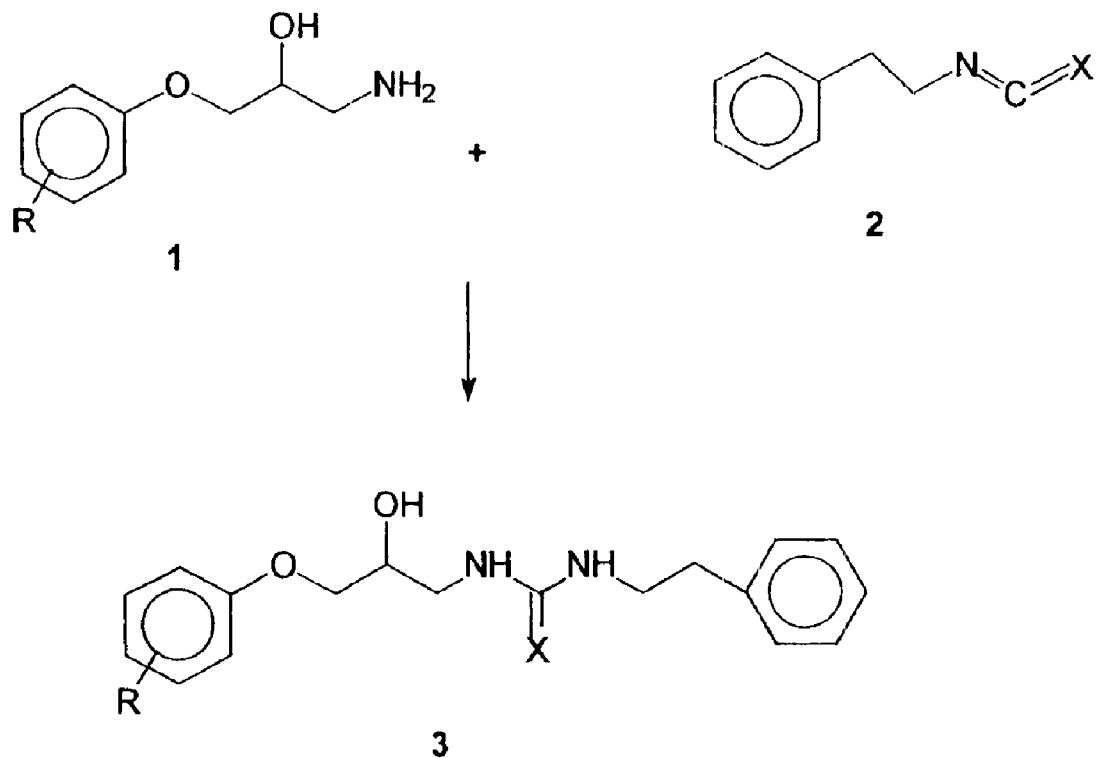

The presently invention relates to novel n-aryloxypropanolyl-N'-phenethyl-urea. The present invention particularly relates to the synthesis of novel N-aryloxypropanolyl-N'-phenethyl-urea derivatives of formula 3 and their use as potent appetite suppressants for treatment of obesity Formula 3

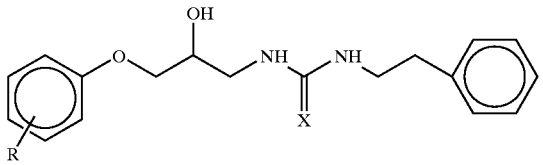

wherein R is selected from the group consisting of H, 2, 3 or 4-trifluoromethyl, 2, 3, or 4-chloro, 2, 3, or 4-bromo, 4-acetyl, 4-propionyl, 4-acetamido, 2,3 or 4 methoxy, 4 nitrile, 2,3 or 4-methyl, and 4 formyl and X is S or O.

BACKGROUND OF INVENTION

Obesity is now a common disorder in the industrialized as well as in the developing countries. It is estimated that somewhere between 34 and 61 million people in the USA are obese and in much of the developing countries the incidence is increasing by about 1% per year. It is responsible for various adverse effects on health being associated with an increase in morbidity and mortality from diabetes, hypertension, cardiovascular diseases and certain forms of cancer.

There are only two drugs currently available for the long term treatment of obesity in United States. One of these, sibutramine (Ryan, D. H., Kaiser, P., Bray, G. A. *Obes. Res.* 1995, 3:553S–9S; Jones, S. P., Smith, I. G., Kelly, F., Gray, J. A. *Int J Obes Relat Metab Disord* 1995, 19:41), the only FDA approved drug, suppresses appetite by altering norepinephrine and 5HT metabolism in the brain. The other drug, orlistat (*Int J Obes Relat Metab disord* 1997, 21:S12–S23), reduces fat absorption by inhibiting gastric, pancreatic and other gastrointestinal lipases. The results of long-term clinical trials, extensive information of clinical effectiveness and side effects, however indicate that both of these drugs are of limited efficacy (Hill, J. O., Haupman, J., Asnderson, J. W. *Am J Clin Nutr* 1999, 69:1108–16; Sjostrom, L., Rissanen, A., Anderson, T. *Lancet* 1998, 352:167–172; Davidson, M. H., Hauptman, J., DiGirolamo, M. etal, *J Am Med Assoc* 1999, 281:235–42; Hollander, P. A., Elbein, S. C., Hirsch, I. B. etal *Diabetes Care* 1998, 21:1288–94; Kaiser, P. E. & Hinson, J. L. J Clin. Pharmacol 1994, 34, 1019; Bray, G. A. *Obes Res* 7, 1999, 189–198; Fanghanel, G., Cortinas, L., Sanchez-Reyes, L., Berber, A., Int. J. Obes. 2000, 24(2), 144–150; Cuellar, Guillermina, Elisa Martinez; Ruiz, Alberto Martinez; Monsalve, Maria Cristina Revilla, Berber, Arturo, Obes. Res. 2000, 8(1), 71–82).

OBJECTS OF THE INVENTION

The main object of the invention is to provide novel N-aryloxypropanolyl-N'-phenethyl ureas useful as appetite suppressant.

Another objective of the invention is to provide a process for the preparation of novel N-aryloxypropanolyl-N'-phenylethyl ureas which are useful as appetite suppressants.

SUMMARY OF THE INVENTION

The present invention relates to the novel N-aryloxypropanolyl-N'-phenylethyl ureas. These compounds are potentially useful in the treatment of obesity.

Accordingly the present invention relates to a novel N-aryloxypropanolyl-N'-phenethyl urea of general formula 3 wherein R is selected from the group consisting of H, 2, 3 or 4-trifluoromethyl, 2, 3, or 4-chloro, 2, 3, or 4-bromo, 4-acetyl, 4-propionyl, 4-acetamido, 2,3 or 4 methoxy, 4 nitrile, 2,3 or 4-methyl and 4-formyl and X is S or O.

Formula 3

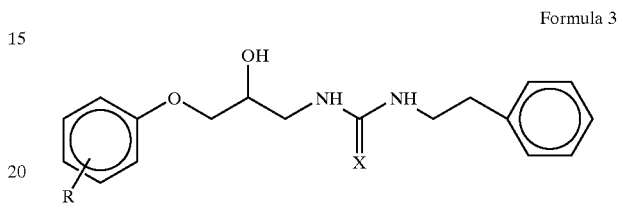

In one embodiment of the invention, representative compounds of formula 3 are selected from the group consisting of:

3a. N-[2-hydroxy-3-(4-trifluoromethylphenoxy)propyl]-N'-2-phenethyl-urea.
3b. N-[2-hydroxy-3-phenoxypropyl]-N'-2-phenethyl-urea.
3c. N-[2-hydroxy-3-(3-trifluoromethylphenoxy)propyl]-N'-2-phenethyl-urea.
3d. N-[3-(4-chlorophenoxy)-2-hydroxypropyl]-N'-2-phenethyl-urea.
3e. N-[3-(4-bromophenoxy)-2-hydroxypropyl]-N'-2-phenethyl-urea.
3f. N-[3-(4-acetylphenoxy)-2-hydroxypropyl]-N'-2-phenethyl-urea.
3g. N-[2-hydroxy-3-(4-propionylphenoxy)propyl]-N'-2-phenethyl-urea.
3h. N-[3-(4-acetamidophenoxy)-2-hydroxypropyl]-N'-2-phenethyl-urea.
3i. N-[2-hydroxy-3-(2-methoxyphenoxy)propyl]-N'-2-phenethyl-urea.
3j. N-[2-hydroxy-3-(4-methoxyphenoxy)propyl]-N'-2-phenethyl-urea.
3k. N-[3-(4-cyanophenoxy)-2-hydroxypropyl]-N'-2-phenethyl-urea.
3l. N-[2-hydroxy-3-(2-methylphenoxy)propyl]-N'-2-phenethyl-urea.
3m. N-[2-hydroxy-3-(3-methoxyphenoxy)propyl]-N'-2-phenethyl-urea.
3n. N-[2-hydroxy-3-(4-trifluoromethylphenoxy)propyl]-N'-2-phenethyl-thiourea.
3o. N-[2-hydroxy-3-(4-propionylphenoxy)propyl]-N'-2-phenethyl-thiourea.
3p. N-[2-hydroxy-3-(4-methoxyphenoxy)propyl]-N'-2-phenethyl-thiourea.

The invention also provides a process for the preparation of N-aryloxypropanolyl-N'-phenethyl urea derivatives of the formula 3 wherein X is S or O and R is selected from the group consisting of H, 2, 3 or 4-trifluoromethyl, 2, 3, or 4-chloro, 2, 3, or 4-bromo, 4-acetyl, 4-propionyl, 4-acetamido, 2,3 or 4 methoxy, 4 nitrile, 2,3 or 4-methyl, and 4-formyl,

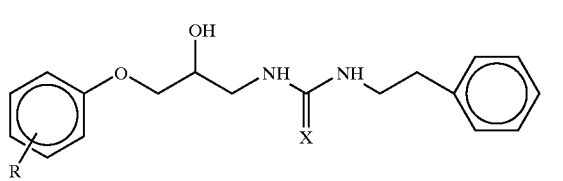

Formula 3 the process comprising reacting a substituted phenolic compound with epichlorohydrin in the presence of alkali carbonate to obtain the corresponding phenoxy epoxy propane which is then reacted with ammonium hydroxide to obtain aminoalcohol of formula 1

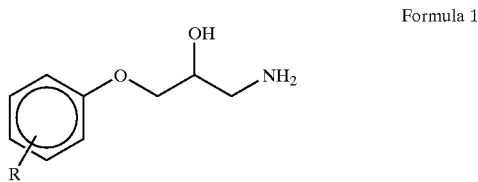

Formula 1 wherein R is as given above, which is then reacted with a cyanate compound of formula 2 wherein X is oxygen or sulphur

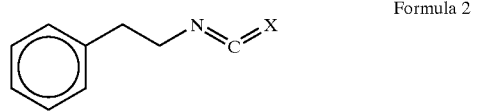

Formula 2 to obtain the compound of formula 3.

In one embodiment of the invention the alkali carbonate is selected from $K_2CO_3$ and $Na_2CO_3$.

In another embodiment of the invention the reaction between compound of formula 1 and compound of formula 2 is carried out in an aprotic solvent selected from the group consisting of $CH_3CN$, $CHCl_3$, $CH_2Cl_2$, THF and 1,2-Dichloroethane.

In another embodiment of the invention the reaction between compound of formula 1 and compound of formula 2 is carried out at a temperature in the range of 15–50° C. for a period ranging between 5–18 hrs.

In another embodiment of the invention the reaction between compound of formula 1 and compound of formula 2 is carried out in equimolar proportions of compound 1 and compound 2.

The present invention also relates to a pharmaceutical composition comprising compound of formula 3 with one or more conventional additives.

The present invention also relates to a method for the treatment of obesity comprising administering to a subject suffering from obesity, a pharmaceutically effective amount of compound of formula 3.

In one embodiment of the invention, the compound of formula 3 is administered in the form of a pharmaceutical composition of compound of formula 3 with pharmaceutically acceptable additives.

The present invention also provides relates to the use of compound of formula 3 alone or with one or more pharmaceutically acceptable excipients for the treatment of obesity.

In another embodiment of the invention, N-[2-hydroxy-3-(4-trifluoromethylphenoxy)propyl]-N'-2-phenethylurea (3a) shows same activity as Sibutramine.

In another embodiment of the invention (N-[2-hydroxy-3-(4-trifluoromethylphenoxy)propyl]-N'-2-phenethyl-urea, showed a decrease of 41.42% in food intake as compared to food intake in the control group.

In another embodiment of the invention, (N-[2-hydroxy-3-(4-methoxyphenoxy)propyl]-N'-2-phenethyl-urea (compound 3j); showed decrease of 31.82% in food intake as compared to food intake in the control group.

In another embodiment of the invention (N-[2-hydroxy-3-(4-trifluoromethylphenoxy)propyl]-N'-2-phenethyl-thiourea (compound 3n), showed decrease of 28.4% in food intake as compared to food intake in the control group.

In another embodiment of the present invention the compound of formula 3 did not cause any significant changes in water intake and gross behaviour.

BRIEF DESCRIPTION OF THE ACCOMPANYING DRAWING

FIG. 1 illustrates the reaction scheme of the process of the invention.

DETAILED DESCRIPTION OF THE INVENTION

The present invention provides a novel N-aryloxypropanolyl-N'-phenethyl urea of general formula 3 wherein R is selected from the group consisting of H, 2, 3 or 4-trifluoromethyl, 2, 3, or 4-chloro, 2, 3, or 4-bromo, 4-acetyl, 4-propionyl, 4-acetamido, 2,3 or 4 methoxy, 4 nitrile, 2,3 or 4-methyl, and 4-formyl and X is S or O.

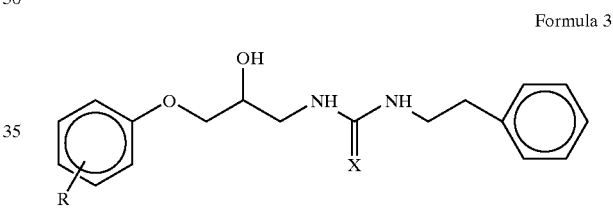

Formula 3

Representative compounds of formula 3 include:
3a. N-[2-hydroxy-3-(4-trifluoromethylphenoxy)propyl]-N'-2-phenethyl-urea.
3b. N-[2-hydroxy-3-phenoxypropyl]-N'-2-phenethyl-urea.
3c. N-[2-hydroxy-3-(3-trifluoromethylphenoxy)propyl]-N'-2-phenethyl-urea.
3d. N-[3-(4-chlorophenoxy)-2-hydroxypropyl]-N'-2-phenethyl-urea.
3e. N-[3-(4-bromophenoxy)-2-hydroxypropyl]-N'-2-phenethyl-urea.
3f. N-[3-(4-acetylphenoxy)-2-hydroxypropyl]-N'-2-phenethyl-urea.
3g. N-[2-hydroxy-3-(4-propionylphenoxy)propyl]-N'-2-phenethyl-urea.
3h. N-[3-(4-acetamidophenoxy)-2-hydroxypropyl]-N'-2-phenethyl-urea.
3i. N-[2-hydroxy-3-(2-methoxyphenoxy)propyl]-N'-2-phenethyl-urea.
3j. N-[2-hydroxy-3-(4-methoxyphenoxy)propyl]-N'-2-phenethyl-urea.
3k. N-[3-(4-cyanophenoxy)-2-hydroxypropyl]-N'-2-phenethyl-urea.
3l. N-[2-hydroxy-3-(2-methylphenoxy)propyl]-N'-2-phenethyl-urea.
3m. N-[2-hydroxy-3-(3-methoxyphenoxy)propyl]-N'-2-phenethyl-urea.
3n. N-[2-hydroxy-3-(4-trifluoromethylphenoxy)propyl]-N'-2-phenethyl-thiourea.

3o. N-[2-hydroxy-3-(4-propionylphenoxy)propyl]-N'-2-phenethyl-thiourea.

3p. N-[2-hydroxy-3-(4-methoxyphenoxy)propyl]-N'-2-phenethyl-thiourea.

The process of preparation of the compound of formula 3 comprises reacting a substituted phenolic compound with epichlorohydrin in the presence of alkali carbonate to obtain the corresponding phenoxy epoxy propane. This is then in turn reacted with ammonium hydroxide to obtain aminoalcohol of formula 1 where R is as given above. The amino alcohol of formula 1 is then reacted with a cyanate compound of formula 2 where X is oxygen or sulphur. This reaction is preferably carried out at a temperature in the range of 15–50° C. for a period ranging between 5–18 hrs. to obtain the compound of formula 3.

The alkali carbonate is selected from $K_2CO_3$ and $Na_2CO_3$ The reaction between compound of formula 1 and compound of formula 2 is carried out in an aprotic solvent such as $CH_3CN$, $CHCl_3$, $CH_2Cl_2$, THF and 1,2-Dichloroethane.

For example, compounds of the formula (3) can conveniently be made according to the general synthetic route outlined in the Scheme given in the accompanying drawing.

The 1-amino-3-aryloxypropan-2-ol of the general formula 1 can be prepared by methods known in the art of preparing analogous compounds eg. by condensing the appropriately substituted phenol with epichlorohydrin in the presence of $K_2CO_3/Na_2CO_3$ to give the corresponding aryloxy epoxy propane which in turn were reacted with $NH_4OH$ to furnish the aminoalcohol of the general formula 1. The process used for this invention comprises of the reaction of one mole equivalent of 1-amino-3-aryloxypropan-2-ol of the general formula 1, R=H, 2,3 or 4-trifluoromethyl, 2,3,4-chloro, 2,3,4-bromo, 4-acetyl, 4-propionyl, 4-acetamido, 2, 3 or 4 methoxy, 4 nitrile, 2,3 or 4-methyl, and 4 formyl with phenylethyl isocyanate (1.5 mole)/phenethylisothiocyanate (1 mole) of the general formula 2, in an aprotic, polar solvent in the temperature range of 25° to 30° C. for a period range of 5 to 15 hrs to give the corresponding urea (X=O)/thiourea (X=S) derivatives of the formula 3 in the accompanying drawing and isolating the compounds by conventional methods.

It was observed that N-[2-hydroxy-3-[4-trifluoromethylphenoxy]propyl]-N'-2-phenethylurea (3a) shows the same activity as Sibutramine. (N-[2-hydroxy-3-(4-trifluoromethylphenoxy)propyl]-N'-2-phenethyl-urea, showed significant decrease of 41.42% in food intake as compared to food intake in control group. (N-[2-hydroxy-3-(4-methoxyphenoxy)propyl]-N'-2-phenethyl-urea (compound 3j), showed significant decrease of 31.82% in food intake as compared to food intake in control group. (N-[2-hydroxy-3-(4-trifluoromethylphenoxy)propyl]-N'-2-phenethyl-thiourea (compound 3n), showed significant decrease of 28.4% in food intake as compared to food intake in control group. The compound of formula 3 did not cause any significant change in water intake and gross behaviour.

The following examples are given by the way of illustration and should not be construed to limit the scope of present invention.

EXAMPLE 1

1-(4-Trifluoromethylphenoxy)-2,3-epoxypropane

A mixture of 4-trifluoromethyl phenol (2 g), $K_2CO_3$ (2.04 g) and epichlorohydrin (10 mL) was stirred at 120° C. for 4 hrs. After completion of reaction, the solid was filtered, filtrate was Diluted with water (50 mL) and extracted with ethylacetate (3×25 mL). Organic layer was washed with Distilled water (3×100 mL) and concentrated to an oil, which was purified on silica gel column using hexane:ethylacetate (9:1) as eluant, to given required compound 2.42 g (90%) yield.

$^1$HNMR (200 MHz, $CDCl_3$): δ 2.75–2.79 (m, 1H, C-3H), 2.90–2.95 (m, 1H, C-3H), 3.34–3.38 (m, 1H, C-2H), 3.93–4.01 (dd, 1H, J=11.0 Hz, J=5.8 Hz, C-1H), 4.26–4.33 (dd, 1H, J=11.1 Hz, J=2.9 Hz, C-1H), 6.96–7.00 (d, 2H, J=8.5 Hz, 2&6-ArH), 7.52–7.57 (d, 2H, J=8.6 Hz, 3&5ArH). MS (m/z): 218 (M$^+$, 100%), 199, 188.

Similarly other substituted aryloxyepoxypropane were prepared substituting the 4-trifluoromethyl phenol by an equivalent amount of substituted phenol (*J. Med. Chem* 1972, 15, No. 3, 286–291.)

EXAMPLE 2

3-Amino-1-(4-trifluoromethylphenoxy)propan-2-ol (1)

A solution of 1-(4-trifluoromethylphenoxy)-2,3-epoxy propane (2 g) in MeOH (10 mL) was stirred with $NH_4OH$ (60 mL) at room temperature (18° C.) for 24 hrs. The turbid solution was filtered through sintered and filtrate was concentrated. The aqueous layer thus obtained was extracted with $CH_2Cl_2$ (3×25 mL). Combined organic extracts dried ($Na_2SO_4$) and concentrated to an oil which solidified, 1.68 g (74%), m.p 75–77° C.

$^1$HNMR (200 MHz, $CDCl_3$): δ 1.18 (bs, 2H, $NH_2$), 2.74–2.95 (m, 2H, $CH_2NH_2$), 3.81–4.03 (m, 4O$CH_2$, $CHOH$ and OH), 6.89–6.93 (d, 2H, J=8:7 Hz, ArH adjacent to 0), 7.45–7.49 (d, 2H, J=8.7 Hz, ArH adjacent to $CF_3$). MS (m/z): 326 ((M+1)$^+$, 100%), 221, 207.

Similarly other substituted phenoxy propanolamines (1a–m) were prepared by substituting the 1-(4-trifluoromethtylphenoxy)-2,3-epoxypropane with an equivalent amount of 1-(substituted phenoxy)-2,3-epoxypropanes, (Terent'ev, A. P.; Volodina, M. A.; Smirnova, M. L.; Mishina, V. G., Zhur. Obshchei Khim. 29, 3478–82, 1959)

EXAMPLE 3

N-[2-Hydroxy-3-(4-trifluoromethylphenoxy)propyl]-N'-2-phenethyl-Urea (3a)

To a stirred solution of 3-amino-1-(4-trifluoromethylphenoxy) propan-2-ol (0.235 g, 1 mmol.) in $CH_3CN$ (5 mL) was added phenylethylisocyanate (0.221 g, 1.5 mmol.) slowly with 15 min. Mixture was stirred at 25° C. for 12 hrs. till all the amine was consumed. Stirring discontinued, solvent distilled off, residual oil was washed with hexane (10 mL). The crude material thus obtained was purified by column chromatography using $CHCl_3$:MeOH (99:1) as the eluant, yield 74%, m.p. 78–80° C.

$^1$HNMR (200 MHz, $CDCl_3$): δ 2.81–2.84 (t, 2H, J=6.7 Hz, ArC$\underline{H}_2$), 3.41–3.48 (m, 4H, N$CH_2$) 3.9–4.2 (m, 3H, OC$\underline{H}_2$C$\underline{H}$OH), 6.93–6.97 (d, 2H, J=8.4 Hz, ArH adjacent to O), 7.16–7.36 (m, 5H, ArH), 7.52–7.56 (d, 2H, J=8.6 Hz, ArH adjacent to $CF_3$) MS (m/z): 383 ((M+1)$^+$, 100%), 329, 236.

EXAMPLE 4

N-[2-Hydroxy-3-phenoxypropyl]-N'-2-phenethylurea (3b)

To a stirred solution of 3-amino-1-phenoxy-propan-2-ol (0.167 g, 1 mmol.) in $CH_3CN$ (5 mL) was added phenylethylisocyanate (0.221 g, 1.5 mmol.) slowly within 15 minutes. Mixture was stirred at 25° C. for 10 hrs. till all the amine was consumed. Stirring discontinued, solid separated was filtered off and washed with hexane (10 mL), dried. Yield 85%, m.p. 108° C.

$^1$HNMR (200 MHz, CDCl$_3$): δ 2.81–2.84 (t, 2H, J=6.8 Hz, ArC$\underline{H}_2$), 3.41–3.50 (m, 4H, NCH$_2$), 3.92–4.1 (m, 3H, OC$\underline{H}_2$—C$\underline{H}$OH), 6.87–6.91 (m, 3H, 2,4,6-OArH), 7.21–7.26 (m, 7H, ArH). MS (m/z): 315 ((M+1)$^+$, 100%), 168.

EXAMPLE 5

N-[2-Hydroxy-3-(3-trifluoromethylphenoxy)propyl]-N'-2-phenethylurea (3c)

To a stirred solution of 3-amino-1-(3-trifluoromethylphenoxy) propan-2-ol (0.235 g, 1 mmol.) in THF (5 mL) was added phenylethylisocyanate (0.221 g, 1.5 mmol.) slowly within 15 min. Mixture was stirred at 24° C. for 12 hrs. till all the amine was consumed. Stirring discontinued, solvent distilled off, residual oil was washed with hexane (10 mL). The crude material thus obtained was purified by column chromatography using CHCl$_3$ as the eluant, yield—33%.

$^1$HNMR (200 MHz, CDCl$_3$): δ 2.78–2.85 (t, 2H, J=6.8 Hz, ArC$\underline{H}_2$), 3.35–3.56 (m, 4H, NCH$_2$), 3.94–4.10 (m, 3H, OC$\underline{H}_2$—C$\underline{H}$—OH), 7.04–7.88 (m, 9H, ArH) MS (m/z): 383 ((M+1)$^+$, 100%), 236.

EXAMPLE 6

N-[3-(4-Chlorophenoxy)-2-hydroxypropyl]-N'-2-phenethyl-urea (3d)

To a stirred solution of 3-amino-1-(4-chlorophenoxy) propan-2-ol (0.2015 g, 1 mmol.) in CH$_3$CN (4 mL) was added phenylethylisocyanate (0.221 g, 1.5 mmol.) slowly within 15 minutes. Mixture was stirred at 26° C. for 10 hrs. till all the amine was consumed. Stirring discontinued, solid separated was filtered off and washed with hexane (10 mL), dried. Yield 41%, m p 100–101° C.

$^1$HNMR (200 MHz, CDCl$_3$): δ 2.77–2.84 (t, 2H, J=6.8 Hz, ArC$\underline{H}_2$), 3.26–3.54 (m, 4H, NCH$_2$), 3.87–4.05 (m, 3H, OC$\underline{H}_2$—C$\underline{H}$—OH), 6.79–6.84 (d, 2H, J=8.9 Hz, ArH adjacent to O), 7.16–7.34 (m, 7 H, ArH). MS (m/z): 351 ((M+1)$^+$, 17%), 349 (M$^+$, 55%).

EXAMPLE 7

N-[3-(4-Bromophenoxy)-2-hydroxypropyl]-N'-2-phenethyl-urea (3e)

To a stirred soln of 3-amino-1-(4-bromophenoxy) propan-2-ol (0.246 g, 1 mmol.) in CH$_3$CN (5 mL) was added phenylethylisocyanate (0.221 g, 1.5 mmol.) slowly within 15 minutes. Mixture was stirred at 27° C. for 5 hrs. till all the amine was consumed. Stirring discontinued, solid separated was filtered off and washed with hexane (10 mL), dried. Yield 57%, m p 115–116° C.

$^1$HNMR (200 MHz, CDCl$_3$): δ 2.77–2.84 (t, 2H, J=6.8 Hz, ArC$\underline{H}_2$), 3.26–3.62 (m, 4H, NCH$_2$), 3.88–4.02 (m, 3H, OC$\underline{H}_2$—C$\underline{H}$—OH), 6.75–6.79 (d, 2H, J=8.7 Hz, ArH adjacent to O), 7.16–7.39 (m, 7H, ArH). MS (m/z): 393 (M$^+$, 100%), 395 ((M+2)$^+$, 97%).

EXAMPLE 8

N-[3-(4-Acetylphenoxy)-2-hydroxypropyl]-N'-2-phenethy-lurea (3f)

To a stirred solution of 3-amino-1-(4-acetylphenoxy) propan-2-ol (0.209 g, 1 mmol.) in 1,2-dichloroethane (5 mL) was added phenylethylisocyanate (0.221 g, 1.5 mmol.) slowly within 15 min. Mixture was stirred at 26° C. for 13 hrs. till all the amine was consumed. Stirring discontinued, solvent distilled off, residual oil was washed with hexane (10 mL). The crude material thus obtained was purified by column chromatography using CHCl$_3$:MeOH (99:1) as the eluant, yield 39%, m.p. 95° C.

$^1$HNMR (200 MHz, CDCl$_3$): δ 2.54- (s, 3H, COCH$_3$), 2.75–2.82 (t, 2H, J=6.6 Hz, ArC$\underline{H}_2$), 3.38–3.47 (m, 4H, NCH$_2$), 4.10–4.24 (m, 3H, OC$\underline{H}_2$—C$\underline{H}$OH), 6.89–6.93 (d, 2H, J=8.6 Hz, ArH adjacent to O), 7.19–7.26 (m, 5H, ArH), 7.88–7.93 (d, 2H, J=8.5 Hz, ArH adjacent to carbonyl gr.) MS (m/z): 357 ((M+1)$^+$, 35%)

EXAMPLE 9

N-[2-Hydroxy-3-(4-propionylphenoxy)propyl]-N'-2-phenethyl-urea (3g)

To a stirred soln of 3-amino-(4-propionylphenoxy) propan-2-ol (0.223 g, 1 mmol.) in CH$_3$CN (5 mL) was added phenylethylisocyanate (0.221 g, 1.5 mmol.) slowly within 15 minutes. Mixture was stirred at 26° C. for 15 hrs. till all the amine was consumed. Stirring discontinued, solid separated was filtered off and washed with hexane (10 mL), dried. Yield 79%, m p 94–95° C.

$^1$HNMR (200 MHz, CDCl$_3$): δ 1.17–1.24- (t, 3H, J=7.3 Hz, CH$_3$), 2.78–2.85 (t, 2H, J=6.8 Hz, ArCH$_2$), 2.89–3.00 (q, 2H, J7.3 Hz, COCH$_2$), 3.43–3.58 (m, 4H, NC$\underline{H}_{2)}$), 3.96–4.05 (m, 3H, OC$\underline{H}_2$—C$\underline{H}$OH)), 6.89–6.94 (d, 2H, J=8.8 Hz, ArH adjacent to O), 7.15–7.77 (m, 5H, ArH), 7.91–7.95 (d, 2H, J=8.8 Hz, ArH adjacent to cabonyl gr) MS (m/z): 371 ((M+1)$^+$, 48%).

EXAMPLE 10

N-[3-(4-Acetamidophenoxy)-2-hydroxypropyl]-N'-2-phenethyl-urea (3h.)

To a stirred soln of 1-(4-acetamidophenoxy)-3-amino propan-2-ol (0.224 g, 1 mmol.) in CH$_3$CN (5 mL) was added phenylethylisocyanate (0.221 g, 1.5 mmol.) slowly within 15 minutes. Mixture was stirred at 25° C. for 11 hrs. till all the amine was consumed. Stirring discontinued, solid separated was filtered off and washed with hexane (10 mL), dried. Yield 64%. m p 150–151° C.

$^1$HNMR (200 MHz, CDCl$_3$): δ 2.11- (s, 3H, COCH$_3$) 2.75–2.82 (t, 2H, J=6.8 Hz, ArC$\underline{H}_2$), 3.28–3.51 (m, 4H, NCH$_2$), 3.87–4.01 (m, 3H, OC$\underline{H}_2$—C$\underline{H}$—OH), 6.81–6.85 (d, 2H, J=8.8 Hz, Ar H adjacent to O), 7.18–7.28 (m, 5H, ArH), 7.40–7.45 (d, 2H, J=8.9 Hz, Ar H adjacent to NH gr) MS (m/z): 372 ((M+1)$^+$, 70%).

EXAMPLE 11

N-[2-Hydroxy-3-(2-methoxyphenoxy)propyl]-N'-2-phenethyl-urea (3i.)

To a stirred solution of 3-amino-1-(2-methoxyphenoxy) propan-2-ol (0.197 g, 1 mmol.) in CH$_3$CN (4 mL) was added phenylethylisocyanate (0.221 g, 1.5 mmol.) slowly within 15 min. Mixture was stirred at 26° C. for 12 hrs. till all the amine was consumed. Stirring discontinued, solvent distilled off, residual oil was washed with hexane (10 mL). The crude material thus obtained was purified by column chromatography using CHCl$_3$:MeOH (98:2) as the eluant, yield 38%, m.p. 80° C.

$^1$HNMR (200 MHz, CDCl$_3$): δ 2.75–2.82 (t, 2H, J=6.8 Hz, ArCH$_2$), 3.33–3.57 (m, 4H, NC $\underline{H}_{2)}$), 3.79 (s, 3H, OCH$_3$), 3.96–4.04 (m, 3H, OC$\underline{H}_2$—C$\underline{H}$OH)), 6.90–6.97 (m, 4H, ArH having OMe gr) 7.16–7.36 (m, 5H, ArH),) MS (m/z): 345 ((M+1)$^+$, 100%).

EXAMPLE 12

N-[2-Hydroxy-3-(4-methoxyphenoxy)propyl]-N'-2-phenethyl-urea (3j)

To a stirred soln of 3-amino-1-(4-methoxyphenoxy) propan-2-ol (0.197 g, 1 mmol.) in CH$_3$CN (4 mL) was added phenylethylisocyanate (0.221 g, 1.5 mmol.) slowly within 15 minutes. Mixture was stirred at 27° C. for 8 hrs. till all the amine was consumed. Stirring discontinued, solid separated was filtered off and washed with hexane (10 mL), dried. Yield—49%. m. p. 90° C.

$^1$HNMR (200 MHz, CDCl$_3$): δ 2.77–2.84 (t, 2H, J=6.7 Hz, ArCH$_2$), 3.42–3.48 (m, 4H, NCH$_2$), 3.76 (s, 3H, OCH$_3$), 3.87–3.90 (d, 2H, J=6.46 Hz, OCH$_2$), 4.00–4.02 (m, 1H, OHC$\underline{H}$), 6.82 (s, 4H, ArH containing OMe gr), 7.15–7.35 (m, 5H, ArH) MS (m/z): 345 ((M+1)$^+$, 100%).

EXAMPLE 13

N-[3-(4-Cyanophenoxy)-2-hydroxypropyl]-N'-2-phenethyl-urea (3k)

To a stirred solution of 3-amino-1-(4-cyanophenoxy) propan-2-ol (0.192 g, 1 mmol.) in 1,2-dichloroethane (5 mL) was added phenylethylisocyanate (0.221 g, 1.5 mmol.) slowly within 15 min. Mixture was stirred at 26° C. for 10 hrs. till all the amine was consumed. Stirring discontinued, solvent distilled off, residual oil was washed with hexane (10 mL). The crude material thus obtained was purified by column chromatography using CHCl$_3$:MeOH (98:2) as the eluant, yield 34%, m.p. 80° C.

$^1$HNMR (200 MHz, CDCl$_3$): δ 2.78–2.85 (t, 2H, J=6.7 Hz, ArC$\underline{H}_2$), 3.28–3.55 (m, 4H, NCH$_2$), 3.95–4.10 (m, 3H, OC$\underline{H}_2$—C$\underline{H}$—OH), 6.92–6.99 (d, 2H, J=8.8 Hz, ArH adjacent to O), 7.16–7.36 (m, 5H, ArH), 7.55–7.60 (d, 2H, J=8.8 Hz, Ar H adjacent to C≡N gr) MS (m/z): 340 ((M+1)$^+$, 93%).

EXAMPLE 14

N-[2-Hydroxy-3-(2-methylphenoxy)propyl]-N'-2-phenethyl-urea (3l.)

To a stirred solution of 3-amino-1-(2-methylphenoxy) propan-2-ol (0.181 g, 1 mmol.) in CH$_3$CN (5 mL) was added phenylethylisocyanate (0.221 g, 1.5 mmol.) slowly within 15 min. Mixture was stirred at 27° C. for 13 hrs. till all the amine was consumed. Stirring discontinued, solvent distilled off, residual oil was washed with hexane (10 mL). The crude material thus obtained was purified by column chromatography using CHCl$_3$ as the eluant, yield—37%.

$^1$HNMR (200 MHz, CDCl$_3$): δ 2.20 (s, 3H, CH$_3$), 2.76–2.83 (t, 2H, J=6.8 Hz, ArCH$_2$), 3.34–3.57 (m, 4H, NCH$_2$), 3.91–4.08 (m, 3H, OC$\underline{H}_2$—C$\underline{H}$—OH), 6.79–6.90 (m, 2H, 4&6 ArH), 7.10–7.32 (m, 7H, ArH). MS (m/z): 329 ((M+1)$^+$, 90%).

EXAMPLE 15

N-[2-Hydroxy-3-(3-methoxyphenoxy)propyl]-N'-2-phenethyl-urea (3m.)

To a stirred solution of 3-amino-1-(3-methoxyphenoxy) propan-2-ol (0.197 g, 1 mmol.) in CH$_3$CN (5 mL) was added phenylethylisocyanate (0.221 g, 1.5 mmol.) slowly within 15 min. Mixture was stirred at 28° C. for 11 hrs. till all the amine was consumed. Stirring discontinued, solvent distilled off, residual oil was washed with hexane (10 mL). The crude material thus obtained was purified by column chromatography using CHCl$_3$:MeOH (99:1) as the eluant, yield 86%, m.p. 83–84° C.

$^1$HNMR (200 MHz, CDCl$_3$): δ 2.77–2.84 (t, 2H, J=6.8 Hz, ArC$\underline{H}_2$) 3.35–3.49 (m, 4H, NCH$_2$)), 3.77 (s, 3H, OCH$_3$), 3.89–3.97 (m, 3H, OC$\underline{H}_2$—C$\underline{H}$OH)), 6.46–6.54 (m, 3H, ArH ortho to O) 7.13–7.30 (m, 6H, ArH),) MS (m/z): 345 ((M+1)$^+$, 100%).

EXAMPLE 16

N-[2-Hydroxy-3-(4-trifluoromethylphenoxy)propyl]-N'-2-phenethyl-thiourea (3n)

To a stirred solution of 3-amino-1-(4-trifluoromethylphenoxy) propan-2-ol (0.235 g, 1 mmol.) in CH$_3$CN (6 mL) was added phenylethylisothiocyanate (0.163 g, 1 mmol.) slowly within 15 min. Mixture was stirred at 25° C. for 8 hrs. till all the amine was consumed Stirring discontinued, solid separated was filtered off and crystallized and recrystallised with dichloromethane and hexane, Yield 64%, m p=127° C.

$^1$HNMR (200 MHz, CDCl$_3$): δ 2.89–2.95 (t, 2H, J=6.82 Hz, ArC$\underline{H}_2$), 3.69–3.8 (m, 4H, NCH$_2$) 3.95–4.02 (m, 2H, OC$\underline{H}_2$), 4.2 (m, 1H, C$\underline{H}$OH), 6.93–6.97 (d, 2H, J=8.7 Hz, ArH adjacent to O), 7.19–7.25 (m, 5H, ArH), 7.53–7.58 (d, 2H, J=8.7 Hz, ArH adjacent to CF$_3$) MS (m/z): 399 ((M+1)$^+$, 93%).

EXAMPLE 17

N-[2-Hydroxy-3-(4-propionylphenoxy)propyl]-N'-2-phenethyl-thiourea (3o)

To a stirred solution of 3-amino-1-(4-propionylphenoxy) propan-2-ol (0.223 g, 1 mmol) in CH$_3$CN (6 mL) was added phenylethylisothiocyanate (0.163 g, 1 mmol.) slowly within 15 min. Mixture was stirred at 26° C. for 9 hrs. till all the amine was consumed. Stirring discontinued, solid separated was filtered off and crystallized and recrystallised with dichloromethane and hexane, Yield 64%, m p=125° C.

$^1$HNMR (200 MHz, CDCl$_3$): δ 1.17–1.24 (t, 3H, J=7.2 Hz, CH$_3$), 2.88–2.99 (m, 4H, COCH$_2$, ArC$\underline{H}_2$), 3.63–3.79 (m, 4H, NCH$_2$)), 3.96–4.08 (m, 2H, OC$\underline{H}_2$), 4.15–4.19 (m, 1H, C$\underline{H}$OH), 6.88–6.93 (d, 2H, J=8.8 Hz, ArH adjacent to O), 7.19–7.33 (m, 5H, ArH), 7.90–7.95 (d, 2H, J=8.8 Hz, Ar H adjacent to cabonyl gr) MS (m/z): 387 ((M+1)$^+$, 100%).

EXAMPLE 18

N-[2-Hydroxy-3-(4-methoxyphenoxy)propyl]-N'-2-phenethyl-thiourea (3p)

To a stirred solution of 3-amino-1-(4-methoxyphenoxy) propan-2-ol (0.197 g, 1 mmol.) in CH$_3$CN (5 mL) was added phenylethylisothiocyanate (0.163 g, 1 mmol.) slowly within 15 min. Mixture was stirred at 26° C. for 9 hrs. till all the amine was consumed Stirring discontinued, solid separated was filtered off and crystallized and recrystallised with dichloromethane and hexane, Yield—72%, m p=74–76° C.

$^1$HNMR (200 MHz, CDCl$_3$): δ 2.87–2.94 (m, 2H, ArC$\underline{H}_2$), 3.58–3.93 (m, 9H, NCH$_2$, OCH$_3$, OCH$_2$), 4.11 (m, 1H, C$\underline{H}$OH)), 6.81–6.82 (s, 4H, ArH containing OMe gr.), 7.22–7.26 (m, 5H, ArH),) MS (m/z): 361 ((M+1)$^+$, 100%).

Advantage

The pharmacological evaluation of the test compounds of general formula 3 was carried out by the following protocol.

The appetite suppressant activity of test compounds was tested on scheduled fed rat model of appetite. The study was conducted in adult male Sprague Dawley rats, weighing 175–200 g on arrival). The animals were housed in transparent cages of Bayer Makrolon type 3118 measuring 425× 266×180 with floor area 800 cm². In each cage one rat was kept. A special fat rich diet (Diet #12451, Research Diets, NJ, USA) was provided only for 3 h (11 am–2 pm) daily [no diet in rest of the period]. Water was provided for 24 h. Diet was weighed prior to and after observation period by an electronic [Digital display] balance. Food intake was recorded by calculating the difference between prior and after weight of diet. Rats were weighed weekly after feeding. Rats were provided 16 g of diet daily and within 12–14 days animals achieved base line food intake (12–14 g) with gain in body weight (230–250 g) indicating adaptation to scheduled feeding. Only those rats that adapted to schedule feeding were used in the study. Rat showing significant less food intake and weight gain as compared to others was excluded from the study.

Thereafter, tests compounds dissolved in 10% DMSO aqueous solution and given in dose of 20 µmol/kg, by oral route. The test compounds were administered 30 min prior to food. Each test compounds were given in 5 rats. Diet and water was weighed at hourly interval in control and compound treated rats. During the period of feeding the gross behavior of rat was also observed.

The significance of difference between the food intake of treated and control groups was determined by unpaired Student's test [Two tailed p value].

The compound 3a, chemically, (N-[2-hydroxy-3-(4-trifluoromethylphenoxy) propyl]-N'-2-phenethyl-urea, showed significant decrease of 41.42% in food intake as compared to food intake in the control group. The compound 3a did not cause any significant change in water intake and gross behaviour. Moreover, the decrease showed by the compound 3a was comparable with the decrease in food intake (38.57%) caused by Sibutramine (20 µmol/kg, by oral route).

The compound 3j, chemically, (N-[2-hydroxy-3-(4-methoxyphenoxy) propyl]-N'-2-phenethyl-urea, showed significant decrease of 31.82% in food intake as compared to food intake in the control group. The compound 3j did not cause any significant change in water intake and gross behaviour.

The compound 3n, chemically, (N-[2-hydroxy-3-(4-trifluoromethylphenoxy) propyl]-N'-2-phenethyl-thiourea, showed significant decrease of 28.4% in food intake as compared to food intake in the control group. The compound 3n did not cause any significant change in water intake and gross behaviour.

The advantage of the present invention is that it provide a new class of compounds which are appetite suppressants and are simple than the existing standard drug sibutramine. The starting materials of the compounds of the present invention are cheap and are easily available. The process described here in simple economically feasible and ecofriendly.

We claim:

1. N-aryloxypropanolyl-N'-phenethyl urea of general formula 3 wherein R is selected from the group consisting of H, 2, 3 or 4-trifluoromethyl, 2, 3, or 4-chloro, 2, 3, or 4-bromo, 4-acetyl, 4-propionyl, 4-acetamido, 2,3 or 4 methoxy, 4 nitrile, 2,3 or 4-methyl, and 4-formyl and X is S or O.

Formula 3

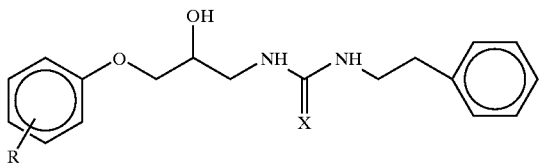

2. A compound of formula 3 as claimed in claim 1 selected from the group consisting of:
3a. N-[2-hydroxy-3-(4-trifluoromethylphenoxy)propyl]-N'-2-phenethyl-urea
3b. N-[2-hydroxy-3-phenoxypropyl]-N'-2-phenethyl-urea
3c. N-[2-hydroxy-3-(3-trifluoromethylphenoxy)propyl]-N'-2-phenethyl-urea
3d. N-[3-(4-chlorophenoxy)-2-hydroxypropyl]-N'-2-phenethyl-urea
3e. N-[3-(4-bromophenoxy)-2-hydroxypropyl]-N'-2-phenethyl-urea
3f. N-[3-(4-acetylphenoxy)-2-hydroxypropyl]-N'-2-phenethyl-urea
3g. N-[2-hydroxy-3-(4-propionylphenoxy)propyl]-N'-2-phenethyl-urea
3h. N-[3-(4-acetamidophenoxy)-2-hydroxypropyl]-N'-2-phenethyl-urea
3i. N-[2-hydroxy-3(2-methoxyphenoxy)propyl]-N'-2-phenethyl-urea
3j. N-[2-hydroxy-3-(4-methoxyphenoxy)propyl]-N'-2-phenethyl-urea
3k. N-[3-(4-cyanophenoxy)-2-hydroxypropyl]-N'-2-phenethyl-urea
3l. N-[2-hydroxy-3-(2-methylphenoxy)propyl]-N'-2-phenethyl-urea
3m. N-[2-hydroxy-3-(3-methoxyphenoxy)propyl]-N'-2-phenethyl-urea
3n. N-[2-hydroxy-3-(4-trifluoromethylphenoxy)propyl]-N'-2-phenethyl-thiourea
3o. N-[2-hydroxy-3-(4-propionylphenoxy)propyl]-N'-2-phenethyl-thiourea
3p. N-[2-hydroxy-3-(4-methoxyphenoxy)propyl]-N'-2-phenethyl-thiourea.

3. A process for the preparation of N-aryloxypropanolyl-N'-phenethyl urea derivatives of the formula 3

Formula 3

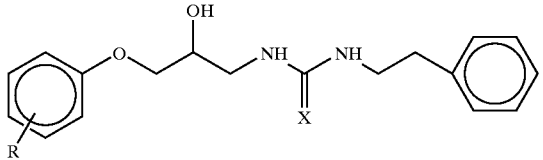

wherein X is S or O and R is selected from the group consisting of H, 2, 3 or 4-trifluoromethyl, 2,3, or 4-chloro, 2, 3, or 4-bromo, 4-acetyl, 4-propionyl, 4-acetamido, 2,3 or 4 methoxy, 4 nitrile, 2,3 or 4-methyl, and 4-formyl, the process comprising reacting a substituted phenolic compound with epichlorohydrin in the presence of alkali carbonate to obtain the corresponding phenoxy epoxy propane which is then reacted with ammonium hydroxide to obtain aminoalcohol of formula 1

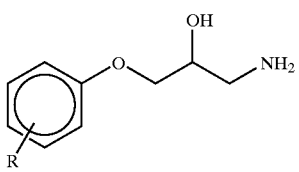

Formula 1 wherein R is given above, which is then reacted with a cyanate compound of formula 2 wherein is oxygen or sulphur

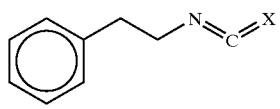

Formula 2 to obtain the compound of formula 3.

4. The process as claimed in claim 3 wherein the alkali carbonate is selected from $K_2CO_3$ and $Na_2CO_3$.

5. The process as claimed in claim 3 wherein the reaction between compound of formula 1 and compound of formula 2 is carried out in an aprotic solvent selected from the group consisting of $CH_3CN$, $CHCl_3$, $CH_2Cl_2$ THF and 1,2-Dichloroethane.

6. The process as claimed in claim 3 wherein the reaction between compound of formula 1 and compound of formula 2 is carried out at a temperature in the range of 15–50° C. for a period ranging between 5–18 hrs.

7. The process as claimed in claim 3 wherein the reaction between the compound of formula 1 and compound of formula 2 is carried out in equimolar proportions of compound 1 and compound 2.

8. A pharmaceutical composition comprising a compound of formula 3 of claim 1 with one or more conventional additives.

9. A method for the treatment of obesity comprising administering to a subject suffering from obesity, a pharmaceutically effective amount of a compound of formula 3 of claim 1.

10. The method as claimed in claim 9 wherein the compound of formula 3 is administered in the form of a pharmaceutical composition of compound of formula 3 with pharmaceutically acceptable additives.

11. The method as claimed in claim 9 wherein the compound of formula 3 is administered alone or with one or more pharmaceutically acceptable excipients.

12. A method for the treatment of obesity comprising administering to a subject suffering from obesity, a pharmaceutically effective amount of a compound of claim 2.

13. The method as claimed in claim 12 wherein N-[2-hydroxy-3-(4-trifluoromethylphenoxy)propyl]-N'-2-phenethylurea (3a) shows same activity as Sibutramine.

14. The method as claimed in claim 12 wherein (N-[2-hydroxy-3-(4-trifluoromethylphenoxy)propyl]-N'-2-phenethyl-urea, showed a decrease of 41.42% in food intake as compared to food intake in the control group.

15. The method as claimed in claim 12 wherein (N-[2-hydroxy-3-(4-methoxyphenoxy)propyl]-N'-2-phenethyl-urea (compound 3j), showed decrease of 3.82% in food intake as compared to food intake in the control group.

16. The method as claimed in claim 12 wherein (N-[2-hydroxy-3-(4-trifluoromethylphenoxy)propyl]-N'-2-phenethyl-thiourea (compound 3n), showed decrease of 28.4% in food intake as compared to food intake in the control group.

* * * * *